US 9,753,160 B2

(12) United States Patent
Bellazzini

(10) Patent No.: US 9,753,160 B2
(45) Date of Patent: Sep. 5, 2017

(54) DIGITAL X-RAY SENSOR

(71) Applicant: Ronaldo Bellazzini, Pisa (IT)

(72) Inventor: Ronaldo Bellazzini, Pisa (IT)

( * ) Notice: Subject to any disclaimer, the term of this patent is extended or adjusted under 35 U.S.C. 154(b) by 473 days.

(21) Appl. No.: 14/399,358

(22) PCT Filed: May 15, 2013

(86) PCT No.: PCT/IB2013/053993
§ 371 (c)(1),
(2) Date: Nov. 6, 2014

(87) PCT Pub. No.: WO2013/190401
PCT Pub. Date: Dec. 27, 2013

(65) Prior Publication Data
US 2015/0139390 A1    May 21, 2015

(30) Foreign Application Priority Data
May 15, 2012    (IT) .............................. PI2012A000060

(51) Int. Cl.
*G01T 1/24*    (2006.01)
*G01N 23/04*    (2006.01)

(52) U.S. Cl.
CPC ............. *G01T 1/247* (2013.01); *G01N 23/04* (2013.01)

(58) Field of Classification Search
CPC ................................ G01T 1/247; G01N 23/04
USPC ..................................................... 250/370.09
See application file for complete search history.

(56) References Cited

U.S. PATENT DOCUMENTS

| 2008/0099689 | A1* | 5/2008 | Nygard | G01T 1/2018 250/370.09 |
| 2010/0329425 | A1* | 12/2010 | Guo | G01T 1/247 378/91 |
| 2014/0185781 | A1* | 7/2014 | Reitz | G01T 7/005 378/207 |
| 2014/0270073 | A1* | 9/2014 | Spahn | G01N 23/04 378/62 |

OTHER PUBLICATIONS

International Search Report mailed Jan. 23, 2014, corresponding to International Patent Application PCT/IB2013/053993.
Sia R et al: "Solid-state photon-counting hybrid detector array for high-resolution multi-energy X-ray imaging", Nuclear Instruments & Methods in Physics Research. Section A: Accelerators Spectrometers, Detectors, and Associated Equipment, vol. 652, No. 1, Feb. 22, 2011. pp. 470-473.
Sindre Mikkelsen et al: "An ASIC for multi-energy x-ray counting", Nuclear Science Symposium Conference Record, 2008, IEEE, Piscataway, NJ, USA, Oct. 19 2008, pp. 1996-2001.
(Continued)

*Primary Examiner* — David Porta
*Assistant Examiner* — Gisselle Gutierrez
(74) *Attorney, Agent, or Firm* — Ladas & Parry LLP

(57) ABSTRACT

A digital X-ray sensor having a detection layer, and a collection layer formed by pixels in the form of a CMOS ASIC, wherein the sensor is provided with a "photon-counting" function and is suitable for radiological applications, so that the best arrangement is obtained between the image quality and the radiation dose absorbed by a subject.

28 Claims, 7 Drawing Sheets

(56) References Cited

OTHER PUBLICATIONS

Llopart X et al: "MEDIPIX2, A 64K Pixel Read Out Chip With 55 Mum Square Elements Working in Single Photon Counting Mode", 2001 IEEE Nuclear Science Symposium Conference Record. / 2001 IEEE Nuclear Science Symposium and Medical Imaging Conference. San Diego, CA, Nov. 4-10, 2001; vol. 3, Nov. 4-10, 2081 (2001-11-84), pp. 1484-1488.

P. Fessler et al: "An ultra low noise multi-channel integrated readout for X-rays multi-detectors", Nuclear Instruments and Methods in Physics Research Section A: Accelerators, Spectrometers, Detectors and Associated Equipment, vol. 346, No. 1-2, Jul. 1, 1994 (Jul. 1, 1994), pp. 213-219.

Matteo Perenzoni et al: "A Multispectral Analog Photon-Counting Readout Circuit for X-ray Hybrid Pixel Detectors", IEEE Transactions on Instrumentation and Measurement, IEEE Service Center, Piscataway, NJ, US, vol. 57, No. 7, Jul. 1, 2008 (Jul. 1, 2008), pp. 1438-1444.

Oelmann B et al: "All-digital window discriminator for photon counting pixel detectors", Electronics Letters, IEE Stevenage, GB, vol. 37, No. 6, Mar. 15, 2001 (Mar. 15, 2001), pp. 373-374.

Roberto Dinapoli et al: "Eiger: Next generation single photon counting detector for X-ray applications" Nuclear Instruments & Methods in Physics Research. Section A: Accelerators, Spectrometers, Detectors, and Associated Equipment, vol. 650, No. 1, 2011, pp. 79-83.

Radicci V et al: "EIGER a new single photon counting detector for X-ray applications: performance of the chip", Journal of Instrumentation, Institute of Physics Publishing, Bristol, GB, vol. 7, No. 2, Feb. 9, 2012 (Feb. 9, 2012), p. C02019.

Kraft P et al: "Characterization and Calibration of Pilatus Detectors", IEEE Transactions on Nuclear Science, IEEE Service Center, New York, NY, US, vol. 56, No. 3, Jun. 1, 2009 (Jun. 1, 2009), pp. 758-764.

\* cited by examiner

DIGITAL X-RAY SENSOR

This application is a 371 of PCT/IB2013/053993, filed on May 15, 2013, which claims priority to Italian Application No. PI2012A000060, filed May 15, 2012.

FIELD OF THE INVENTION

The present invention relates to a digital X-ray sensor for diagnostic and analytical purposes, which is provided with a "photon-counting" function.

BACKGROUND OF THE INVENTION

Digital X-ray sensors exist comprising a conversion layer in the form of an amorphous coating, normally made of Amorphous Selenium or of Cesium iodide, and an integration panel, i.e. a collection layer, that has a TFT pixel structure (Thin Film Transistor). The conversion layer serves for transforming into an electric charge the photons of an X-ray beam that has travelled across an irradiated sample. This may occur directly or indirectly, as in the case of amorphous Selenium and of Cesium iodide; respectively. The total charge obtained by the conversion during an X-ray exposure builds up in the pixels of the integration panel.

Once the exposure has been completed, the amount of charge accumulated in each pixel is read. More in detail, an image acquisition electronics is provided that comprises an analog-to-digital converter arranged at the boundary of the integration panel. The analog-to-digital converter changes the overall charge accumulated in each pixel into an electric voltage, i.e. into a number that is proportional to the overall radiation that has travelled across the sample at each pixel of the integration panel. These numbers can be converted into a radiographic image in which the contrast depends upon the overall radiation that is accumulated in each pixel.

A so-called "photon-counting" technique is also known, in which the photons are counted one-by-one, and are ranked into a plurality of channels, thus obtaining a "film grade" resolution, i.e. a resolution that is comparable with the resolution allowed by high-resolution radiographic plates. In particular, hybrid detectors exist that are known as MediPix and that are provided with an ASIC for carrying out a photon-counting procedure. These hybrid detectors comprise discriminators associated with event counters that are used in such a way that the image acquisition electronics counts only events, i.e. acquisitions of photons that fall in a predetermined energy window. This way, an X-ray imaging technique is obtained that has spectroscopic features. A more recent device, known as Medipix-3, has a finer energy resolution thanks to a real-time charge share correction. Medipix 3 also comprises multiple pixel counters that can be used in different operation modes. This allows a continuous detection, and up to eight energy thresholds can be obtained.

In the Medipix device, like in other devices, the collection layer is implemented by CMOS technology, which is a low-power consumption technology, i.e. about a few Watts, and a low-cost technology. For this reason, the CMOS technology is preferred, in particular, to provide ASICs consisting of a large number of pixels, e.g. about $10^6$, as it is required for a radiological device.

However, as well known, CMOS-based devices are inherently non-calibrated devices. In other words, the units consisting of discriminators/counters of this type cannot provide homogeneous counting responses. In fact, each CMOS counting chain has its own offset value that, moreover, may depend upon environmental conditions such as the temperature, and other operating conditions. A counter associated with a discriminator that has an offset value nearer to the threshold associated with it counts more events than a counter that is associated with a discriminator that has an offset farther from the threshold of the same nominal value. For this reason, an ASIC suitable for the invention, which is implemented by CMOS technology, can give rise to a non-homogeneous response, within a same pixel and from a pixel to another.

Another remarkable drawback of the prior art is that various sources of noise exist. In addition to quantum noise, which is unavoidably related to the intensity of the X-ray beam, a certain level of additional noise is always present, which depends upon the sensor and upon the detection electronics, in particular it depends upon the means used for amplifying the charge. Total, quantum and additional noise prevents the collection pixels from detecting the charge delivered by the conversion layer, when the charge is lower than a predetermined threshold. Therefore, the need is felt that each pixel should contain as much charge as possible, and/or that the noise should be substantially reduced to the quantum level only, so that each pixel can work if it is reached by a minimum charge amount.

In the light of the above, a digital sensor formed by pixels must carry out corrections, or calibrations, in order to limit or avoid some drawbacks due to the sensor itself or to the technology on which the read electronics (ASIC) is based. The main effects that must be corrected are:

- the occurrence of a "dark current" generated by the sensor, i.e. an intrinsic current that can be detected in the absence of any outer irradiation and of strong collector electric fields. The dark current is one of the most important components of additional noise, in addition to quantum noise;
- an offset of the direct current level at the outlet of the inlet stage, i.e. of the pre-amplification stage, and of the gain stage of the pixel electronics;
- an offset of the direct current level at the inlet of the discriminator/counter unit.

Sindre Mikkelsen et al.[1] describe a radiography sensor comprising an X-ray-sensitive conversion layer and a 64-pixel ASIC collector, provided with a photon-counting function. Each pixel of the ASIC has a single inlet terminal that is normally connected to an electrode of the radiation sensor. In an example, which discloses a calibration function, each pixel is connected to a common calibration node through a switch controlled by a software outside of the ASIC, and a calibration network is provided, i.e. an adjustment means, that enables a user to switch the inlet terminal of each pixel from a pad of the sensor pixel to the calibration node. Therefore, this sensor is configured for executing a sequential calibration, i.e. a pixel-by-pixel calibration, under the control of the software. Such a calibration technique cannot practically be used in the case of a matrix that has a large number of pixels, since the pixel-by-pixel calibration would need a too long calibration time, in comparison to the requirements, for instance, of a radiological sensor that must carry out a large number of radiological sessions within a prefixed time.

Dinapoli et al.[2], and Radicci et al.[3] describe a similar radiography sensor provided with a manual calibration circuit. This circuit is configured for working in a test mode, in which a known amount of charge is supplied to the inlet of an amplifier of a predetermined pixel. The response of the amplifier of the selected pixel is available to be shown by a display device like an oscilloscope. In particular, a precise calibration of the chip is carried out with a monochromatic X-ray source once the collection chip has been connected to the photon-sensitive layer by a bump-bonding technique. Also in this case, the calibration is carried out pixel-by-pixel. Moreover, the calibration has to be carried out manually by an operator, and, consequently, the technique cannot be readily used for matrices that comprise a large number of pixels.

Perenzoni et al.[4] describe a reading circuit configured for carrying out a photon-counting function for a radiography sensor formed by pixel, in which a completely analog self-calibration procedure is provided. An analog self-calibration must be repeated before each photon capture event in the same conditions as in the normal operation. Therefore, the noise that occurs during the calibration procedure has the same level as the noise that occurs while receiving the data from the sample, so the noise of the calibration procedure is added to the noise of the normal operation.

Devices like the above-mentioned Medipix have further drawbacks. In particular, they do not allow making a surface larger than 14×14 mm, whereby 256×256 pixels can be provided at most. Furthermore, the pixels are arranged in a square grid. Such an arrangement is not the best suited for sampling the radiation field, since it leads to a worse sampling out of the directions of a couple of orthogonal axis. Finally, Medipix has been conceived to be preferably coupled with Silicon converters, in which the photon-to-charge conversion is carried out at a very low efficiency if the photon energy is higher than 15 keV. These drawbacks do not allow using such devices as Medipix to make medical radiology sensors. Briefly, sensors cannot be provided that have a continuous active surface large enough and a sensitivity to X-ray energy high enough for this purpose.

Another important drawback of the prior art is the low conversion efficiency of the conversion layer. Selenium converters are known that have a thickness not larger than 0.5 mm. These converters, due to the relatively low atomic number of Selenium, are sensitive to X-ray beams up to a maximum energy of about 30-40 keV only. Further Caesium iodide converters, even if manufactured with a suitable thickness, are however affected by a resolution loss, due to the indirect X-ray beam-to-charge conversion process. It is therefore desirable to provide a digital X-ray sensor that has a high efficiency, and a low-noise conversion layer, by which a "film grade" resolution can be obtained.

Further, so-called integration techniques are available on surfaces that allow their use in medical radiology, as in the case of WO96/33424. However, such integration techniques are not suitable for ranking the photons converted during a same flash according to the energy that the photons possess when they reach the conversion layer. This feature, which is also known as the "colour" of the photons, can be very relevant in some diagnostic and analytic procedures. By the known integration techniques, however, the "colour" can be obtained by carrying out so many flashes as the number of the energy levels of interest, and by changing in turn the energy of the X-ray beam. Besides taking a long time and requiring a large amount of resources, this technique would expose a living subject to a strong dose of harmful radiation.

SUMMARY OF THE INVENTION

It is therefore a feature of the present invention to provide a digital X-ray sensor comprising a detection layer, i.e. a conversion layer, and a collection layer formed by pixels in the form of a CMOS ASIC, wherein the sensor is provided with a "photon-counting" function and is suitable for radiological applications, in particular with a "film grade" resolution, so that the best arrangement is obtained between the image quality and the radiation dose absorbed by a subject.

It is a particular feature of the present invention to provide such a digital sensor in which the collection layer comprises more pixels than the prior art CMOS devices, in particular $10^6$ pixels, in order to form continuous active surfaces of at least some square centimeters, as required for radiological sensors.

It is also a feature of the present invention to provide such a sensor for performing corrections, i.e. calibration procedures to take into account the effects of the use of CMOS technology, thus avoiding long and expensive manual and/or computation procedures.

It is a particular feature of the present invention to provide such a radiography sensor that has an overall residual noise lower than the prior art sensors, in particular to provide a digital X-ray sensor in which a additional noise does not substantially occur, and which allows the most efficient use of relatively low X-ray doses.

It is another feature of the invention to provide such a sensor for considerably increasing the information of the images generated, for instance, in bone densitometry and mammography applications.

It is also a feature of the invention to provide such a sensor that can provide a very high spatial resolution, in order to improve image sharpness.

It is also a feature of the invention to provide a digital X-ray sensor that allows, by a same radiation dose, a contrast resolution better than in the prior art sensors, i.e. a sensor that allows to distinguish more clearly slightly different grey tones, or to provide a sensor that allows the same contrast resolution by a less strong X-ray dose, with respect to the prior art sensors.

It is a further feature of the invention to provide a digital X-ray sensor that allows a high frame rate, i.e. a frame rate even higher than 100 frames/sec, and that can therefore detect multiple images for "slot-scanning" applications in about one second.

It is a particular feature of the present invention to provide a radiography sensor that comprises a conversion layer and a reading electronics that allow measuring photons in an energy window wider than in the prior art sensors.

It is another particular feature of the present invention to provide a radiography sensor in which the conversion layer allows collecting an amount of electrons per absorbed photon larger than in the prior art.

These and other objects are achieved by a digital X-ray sensor comprising:
- a semiconductor conversion layer, configured for receiving X-ray photons and for converting the X-ray photons into an electric charge;
- a semiconductor collection layer integrated with the conversion layer, the collection layer formed by a plurality of collection pixels that are arranged in a predetermined pattern, each collection pixel of the collection layer configured for receiving electrons from the conversion layer;
- a data output means for transferring the data collected by the collection pixels to an acquisition electronics;

wherein
  in each collection pixel a charge amplification means is contained that is arranged for receiving an electric charge as an inlet charge, which comprises the electrons produced by the conversion layer, the amplification means configured for generating a voltage signal that has a peak value proportional to the inlet electric charge, in each collection pixel a plurality of N window discriminators is contained, each discriminator ($24_j$) configured for:
carrying out a comparison between said peak value and two charge threshold values comprising a lower threshold value and an upper threshold value, and
carrying out an instantaneous transition between a 0-level and a 1-level if:
said peak value is higher than said lower threshold value;
said peak value is lower than said upper threshold value;
wherein, for each discriminator of said N discriminators, at least one condition occurs that is selected between:
the upper threshold value is lower than the lower threshold value of at least one of said discriminators distinct from said each discriminator, in particular the upper threshold value is equal to the lower threshold value of said at least one of the discriminators distinct from said each discriminator,
the lower threshold value is higher than the lower threshold value of at least one of the discriminators distinct from said each discriminator, in particular the lower threshold value is equal to the upper threshold value of said at least one of the discriminators distinct from said each discriminator,
wherein a plurality of N counters is contained in each collection pixel, each of which is associated with a respective discriminator,
wherein each counter is configured to increase by 1 unit a value of an own counting if:
the peak value is higher than the lower threshold value of the respective discriminator, and
the peak value is lower than the upper threshold value of the respective discriminator,
while the counters distinct from said each counter are configured for keeping unchanged the own count value,
wherein the data output means is configured for receiving from each collection pixel measurement data of the radiation incident in N "colours" corresponding to the counts stored in N energy windows for each charge threshold.

Advantageously, the data output means is configured for receiving from each collection pixel measurement data of the radiation incident in N "colours" corresponding to the counts stored in N energy windows for each charge threshold.

A calibration means can be provided for calibrating each collection pixel, in particular each discriminator/counter unit, said calibration means comprising, in each of said collection pixels:
a DAC, i.e. a digital-to-analog converter, for at least one discriminator of each pixel of the collection layer, configured for receiving combinations of a predetermined number of bits and for generating current values corresponding to the combinations of bits;
a current supply means configured for supplying current to the amplification means of each collection pixels;
a logical means resident in each collection pixels, said logical means configured for executing a procedure of computing an offset correction current value.

Advantageously, said logical means is configured for carrying out an iterative procedure of computing an offset correction current value, comprising the steps of:
generating the combinations of bits;
transferring the combinations of bits to the digital-to-analog converter such that the digital-to-analog converter generates a corresponding trial current value;
causing the trial current to be supplied to the amplification means through the supply means;
receiving a count value of the counter;
repeating the above steps if the count value increases due to the trial current;
defining the trial current value as the correction current value, if the count value does not increase due to the trial current.

Advantageously, the charge amplification means, the window discriminators, the counters, the digital-to-analog converter comprise CMOS transistors.

Advantageously, each collection pixels comprises a memory unit for the offset correction current value, and the logical means is also configured for storing the correction current value into the memory unit.

Advantageously, the sensor comprises a means for simultaneously actuating the calibration means of all the collection pixels, such that the iterative procedure is carried out at the same time for each counter, and said correction current is supplied to each collection pixel during an operating step of said sensor.

The digital self-calibration technique, according to the invention, makes it possible to store into the memory unit of each pixel the respective offset correction current that must be steadily injected into each pixel in order to operate the whole sensor in calibration conditions, i.e., such that homogeneous responses are obtained from all the pixel. The correction current remains available for a subsequent long-lasting use.

For example, the self-calibration can be made once, at any instant, and preferably when the sensor is turned on, or at the beginning of each radiography session or before each flash. For this reason, the self-calibration can be carried out at a much lower gain and passband, with respect to prior art analog calibration techniques, therefore with a slight noise. More in general, the self-calibration step can be repeated only in case of significant changes of the environmental and operating conditions.

As indicated above, a calibration procedure carried out conventionally on a matrix comprising a number of pixels, which is suitable, for example, for radiological purposes, would take an unacceptably long time for calibrating pixel-by-pixel each discriminator/counter unit of each pixel of the sensor. For this reason, it is possible to use sensors consisting of modules that have a size larger than those of the prior art, and that comprise each $10^5$ pixel, as an order of magnitude, and therefore comprise each $10^5$-$10^6$ counters to be calibrated. The self-calibration procedure levels the response of all the discriminator of all the pixels in a time of a few milliseconds.

The compensation/correction means for the whole chain of these effects is present in each pixel, and is configured for supplying a compensation direct current to the inlet of the pixel, typically to a pad or to a metal pad connected to a respective metal pad of the conversion layer, upstream of the charge amplification means of the pixel electronics. The value of the trial direct current supplied during the compensation procedure is numerically controlled by the DAC.

Moreover, the final value of the trial direct current, which is specific for each pixel, makes it possible to reduce the "dark current" and, therefore, to reduce the overall noise of the sensor and of the detection electronics. This increases the sensitivity of the sensor and allows a reduction of the radiation doses, which is an important advantage in radiology imaging.

The resolution of the compensation, i.e. the response homogeneity of the pixel, is predetermined only by the number of bits of the DAC. The final current value can be obtained by running a successive approximation algorithm. This algorithm is resident in each pixel, unlike the sensors of the prior art, in which the logical and computation means that runs the calibration algorithm is resident in a unit outside of the pixel, or even in a unit outside of the ASIC. In other words, the algorithm is coded in each pixel, therefore it can be run at the same time in each pixel independently from one another pixel. The value of the direct final current is numerically coded and stored in each pixel. It can be read from outside for statistic purposes, or for adjusting/optimizing the required correction range.

Advantageously, said trial current has a value that decreases at each iteration of said steps of said iterative procedure, starting from an initial trial current value adapted to cause a count event in each discriminator/counter unit, until a final trial current value is attained that does not cause a count event in this discriminator/counter unit. In other words, the logical means of the calibration means is configured for:

supplying a current of decreasing intensity to each pixel, i.e. to the charge amplification means of each pixel, starting from the initial trial current value adapted to cause a count event in each discriminator/counter unit;

checking, for each intensity current value supplied to a pixel, whether each discriminator/counter unit of the collection pixel is carrying out a step of counting;

identifying, for each collection pixel, a maximum supplied current intensity that does not cause a counting event, and storing this maximum current intensity supplied, which does not cause a counting event, as the offset correction current value into the memory unit of the pixel, to be supplied to each discriminator/counter unit in a subsequent operation of the sensor.

Preferably, the calibration procedure carried out by the logical means of the calibration means is a so-called "high/low" procedure, wherein:

the initial trial current value is equal to the maximum current value that can be obtained by the DAC, i.e. to the current value that can be obtained by the DAC set at its own maximum value, this current value adapted to cause a count event in each discriminator/counter unit once the threshold has been set to a minimum value that corresponds to a ground reference of the discriminator/counter unit;

the logical means of the calibration means is configured for causing a subsequent trial current to be supplied to each pixel, said subsequent trial current having:

an intensity lower than a previous trial current, if the previous trial current causes a count event in each discriminator/counter unit;

an intensity higher than a previous trial current, if the previous trial current does not cause a count event in each discriminator/counter unit;

the logical means of the calibration means is configured for storing a trial current value that cannot cause a count event in a discriminator/counter unit, in particular the first supplied trial current value, as the correction current to be supplied to each discriminator/counter unit in a subsequent operation.

In other words, the self-calibration means is configured for supplying currents of progressively decreasing intensity until the correction current is identified, for each discriminator/counter unit, as the maximum trial current that does not cause a count event by the discriminator/counter unit. This way, the offset of the discriminator/counter unit is shifted to the maximum value that is still lower than the threshold.

The high/low technique reduces the number of trial current values required to carry out the calibration step.

In particular, the self-calibration means comprises a 5-bit DAC, therefore this maximum predetermined value is 32. In this case, the self-calibration time can be is estimated as a few milliseconds.

Thanks to the sensor according to the invention, it is possible to remarkably reduce the discrimination threshold of the counters of the pixels of the ASIC, and to bring it to a value as close as possible to the minimum threshold required to discriminate the noise produced by the inlet amplifier. For instance, with a Cadmium telluride conversion layer, this threshold may be about 200 electrons, which corresponds to 1 keV, while with a Silicon conversion layer the threshold may be about 0.8 keV.

The "photon-counting" function of the ASIC is necessary, but not sufficient for ranking the photons according to their energy level. The ranking is allowed by introducing an energy measurement function to the structure of the ASIC. By this function, in each pixel, the electronics of the ASIC can count how many photons have been received, and how many of them have an energy level falling within the different ranges, i.e. within the different energy windows.

Thanks to the sensor according to the invention, as defined above, a plurality of images can be obtained, each related to a single photon energy window, by a same X-ray exposure of a subject, i.e. by subjecting the subject to one radiation dose only. This plurality of images makes it possible to class the observed sample or the subject according to the absorbing power the sample or the subject has with respect to photons of different energy levels.

For instance, the energy windows may define photon energy values set between 5 and 15 keV; 15 and 25 keV; 25 and 40 keV; 40 and 60 keV, and the like.

For instance, the counters may comprise ordinary 15-bit silicon registers, which are configured for counting $2^{15}-1$ photons. By the prior art sensors, it would be necessary to expose the subject to so many flashes as the energy levels the images should relate to. Therefore, for obtaining a same radiological information, the sensor according to the invention reduces the subject's exposure to harmful radiations, with respect to the sensors of the prior art.

For instance, the surface of a sensor or of an elementary block may have a size between 2 and 4 cm, in particular a size of about 2.5×3.0 cm. In this case, the sensor can comprise 476×512=243712 collection pixels, on which about 1 million of multi-channels can be arranged. With such an elementary block size, a common 24×2.5 cm slot can be covered by 8 elementary blocks.

Preferably, the collection pixels have a hexagonal plan shape, and are arranged in a honeycomb pattern. By honeycomb pattern a structure is meant in which a first hexagon is placed adjacent to six further hexagons equal to the first hexagon, each having a side parallel to a respective side of the first hexagon. With respect, for instance, to a square pattern, the honeycomb structure increases the number of pixels per unit area. The honeycomb pattern also allows a spatial resolution that is substantially the same in all the directions. In a square pattern, on the contrary, the resolution along the directions of the diagonal lines of the square is about 40% lower than along the directions of the sides of the square.

In an aspect of the invention, the semiconductor conversion layer comprises a plurality of conversion pixels that are arranged in a pattern corresponding to the pattern of the collection pixels of the collection layer, wherein each conversion pixel univocally corresponds to a respective collection pixel, and an electric connection is provided between each converter pixel and the respective collection pixel.

In an exemplary embodiment, the conversion layer is made of a crystalline material.

In particular the crystalline layer has a metallization layer facing the collection layer which has a pixel structure. This allows maximizing the charge generated by the conversion of each photon, in other words it is possible to enhance the number of electrons that can travel across the conversion layer, so that the noise threshold of the pixel of the ASIC can be easily exceeded.

In particular, the pixels of the conversion layer, which face the pixels of the collection layer, are obtained by a photolithographic technique which may comprise a step of depositing and patterning metal, semiconductor and insulating thin films, similarly to the technique used for making the collection layer pixels.

In an exemplary embodiment of the invention, the conversion layer is joined pixel-by-pixel with the collection layer by a bump-bonding technique, i.e. through a plurality of bumps made of an electrically conductive material located between the conversion layer and the collection layer, wherein each bump is arranged at a respective collection pixel. For instance, the electrically conductive material is an Indium-Bismuth alloy. The bump-bonding technique allows connecting relatively easily the collection layer and the conversion layer, in such a way that each pixel of the conversion layer is electrically connected to the corresponding pixel of the collection layer.

More in detail, the small spheres, i.e. the bumps, may be obtained by depositing respective amounts of the electrically conductive material on a top metal layer of the ASIC of the collection layer.

As an alternative, or in addition, the bumps may be obtained, at each pixel of the ASIC, by a step of growing this amount of electrically conductive material, or by a photolithographic technique, in a post-treatment of the ASIC.

The connection, i.e. the bond, between the collection layer comprising the bumps, and the conversion layer having a pixel structure, may be carried out by mutually overlapping and centering the conversion layer and the collection layer, and by a subsequent step of pressing or heating, in order to melt the bumps and form the connection, as it is well known in the art.

In alternative, the semiconductor conversion layer is a coating conversion layer, obtained by a technique of evaporation and/or deposition of a polycrystalline or amorphous semiconductor material on the collection layer. These procedures allow to easily forming a detection layer in which the pixels are arranged according to the same pattern as the ASIC, i.e. as the pixel of the collection layer. High-performance ASICs are advantageous if relatively low-charge-efficiency conversion layers are used, as in the case of amorphous coating conversion layers, which allow making low-cost the conversion layers.

In particular, the amorphous material may comprise semiconductor materials such as cadmium telluride; selenium; lead iodide; mercuric iodide; gallium arsenide; germanium, or a combination of these materials.

In particular the amorphous coating conversion layer may be obtained by a screen-printing technique.

The coating conversion layer provides makes it possible to make a relatively low-cost sensor.

The pixels of the collection layer may have a size set between 300 µm and 25 µm, in particular they may have a size set between 150 µm and 25 µm, more in particular, they may have a size set between 75 µm and 25 µm. The size of the pixels, for a given application, is selected as to obtain an arrangement between the resolution, which requires small pixels, and the number of colours, which generally requires larger pixels, in order to house the required electronics. For instance, if the ASIC is made by a common 0.18-µm CMOS technology, one can assume:
- 200-µm collection pixels, which are normally used in general radiology applications, provided with discriminators and counters for eight energy windows;
- 100-µm collection pixels, which are more than satisfactory for most radiological applications, provided with discriminators and counters for six energy windows;
- 50-µm collection pixels, provided with discriminators and counters for two energy windows.

For instance, if the ASIC is made by a more advanced 0.045-µm CMOS technology, one can assume:
- 200-µm collection pixels, provided with discriminators and counters for thirty-two energy window;
- 100-µm collection pixels, provided with discriminators and counters for sixteen energy windows;
- 50-µm collection pixels, provided with discriminators and counters for eight energy windows.

Advantageously, the sensor comprises a conversion layer cooling means, configured for bringing and maintaining the conversion layer, in use, to/at a temperature lower than a predetermined maximum operation temperature. In particular, the cooling means is configured for bringing and maintaining the conversion layer between 20° C. and 40° C. These temperature values are suitable, in particular, for a Cadmium telluride conversion layer. In use, the ASIC of the collection layer works at a temperature normally set between 50 and 70° C. If no cooling means is provided for the conversion layer, this would reach the operating temperature of the collection layer. However, such a temperature causes a noisy operation of the conversion layer, which obliges to raise the threshold of the latter, and limits therefore its sensitivity, in particular, to low-energy photons.

In fact, a noise threshold exists that would not allow measuring the charge delivered by the converter substrate, if the substrate delivers a small amount of charge. Therefore, it is necessary that the pixel receives as much charge as possible and, moreover, that the converter is so effective that also low-energy photons produce enough charge to exceed the threshold. In any case, the residual noise cannot be reduced to zero.

The cooling means may comprise a Peltier cell arranged with its cold face in contact with the face of the collection layer opposite to the face by which the latter is connected with the conversion layer. This way, the Peltier cell can be associated with conventional air or liquid cooling means for cooling the hot face of the cell.

In a preferred exemplary embodiment, the collection layer has a conductive pad, preferably an aluminium pad, for each collection pixel. In particular, the pad forms an interface to the charge amplifier of the inlet stage of the electronics of each pixel. This is particularly advantageous in the case of a conversion layer obtained by an evaporation/deposition technique of a polycrystalline conversion layer, which may be made of CdTe, since the deposit of the material on the pad allows an easy contact between the conversion layer and the collection layer.

Advantageously, the sensor comprises a means for creating an electric field within the collection layer, said means comprising a first metal thin film arranged, possibly by deposition, about the sensor and configured for being brought to a first predetermined voltage, and a second thin film preferably arranged, possibly by deposition, on the face of the conversion layer connected to the collection layer, such that it is brought to the same voltage as the inlet pads of the conversion layer, normally a voltage of a few Volts. The sign of the voltage on the upper layer is negative or positive according to whether one wishes to collect negative or positive charges on the metalized surface of the lower layer, respectively.

In particular, the second thin film, or various metal film layers deposited on the pixels side of the conversion layer, serves to provide an electric junction that allows the passage of a current of one predetermined sign, while it blocks the passage of the current of the opposite polarity. If a negative charge is collected at the pixels, the junction allows the passage of a negative current created by the collection of the electrons produced by the conversion of the photons, but blocks the passage of negative charge from the outside into the conversion layer. This can be a positive polarity current generated by the extraction of charge from the metals that form the joint. This makes it possible to limit the so-called "dark current".

In an exemplary embodiment, the second thin film, and preferably also further possible metal films deposited on a same face of the conversion layer, are configured to provide a Schottky type junction.

According to another aspect of the invention, a radiographic imaging method is provided by an X-ray sensor according to claim 27.

BRIEF DESCRIPTION OF THE DRAWINGS

The invention will be now shown with the following description of an exemplary embodiment thereof, exemplifying but not limitative, with reference to the attached drawings in which.

DESCRIPTION OF PREFERRED EXEMPLARY EMBODIMENTS

Figure 1:
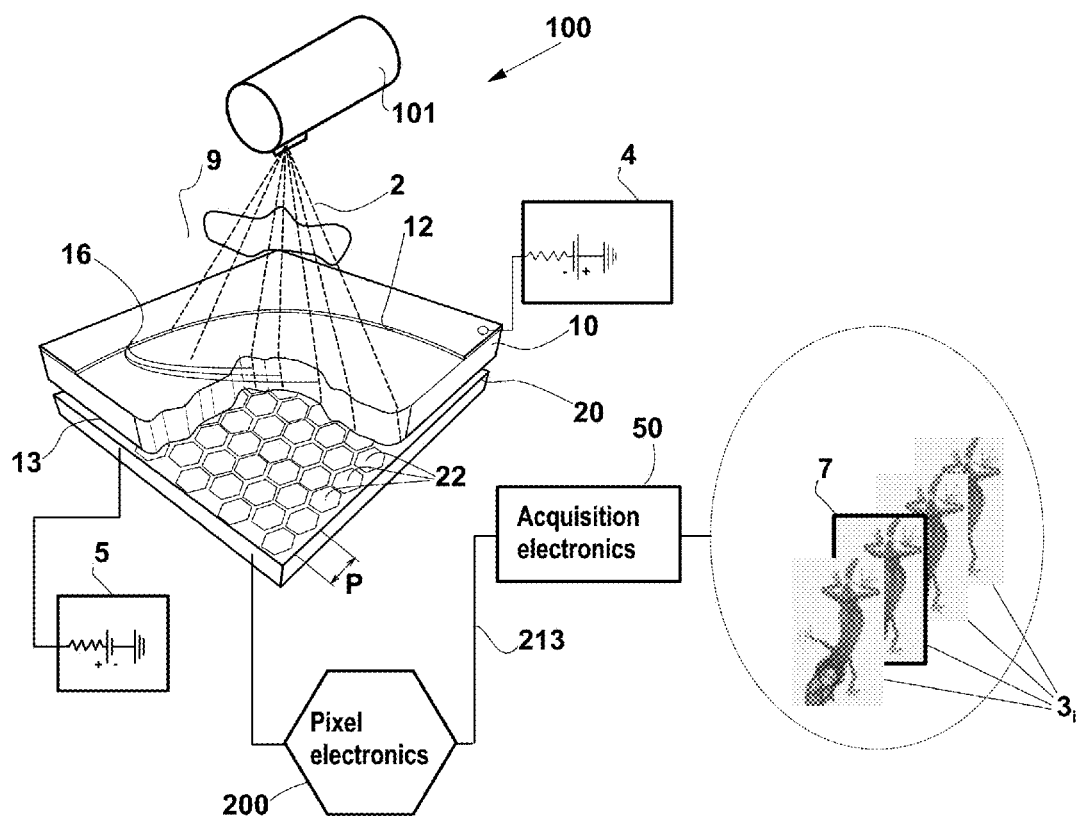
FIG. 1 is a diagram that shows the operation of the sensor according to the invention, and that diagrammatically shows the structure of the sensor itself.

With reference to FIG. 1, a digital X-ray sensor 100 is described, according to an exemplary embodiment of the invention, which comprises a semiconductor conversion layer 10 and a semiconductor collection layer 20.

Conversion layer 10 is arranged to receive X-ray photons 2 from a conventional X-ray source 101, and to convert photons 2 into electrons that form an electric charge 16.

Collection layer 20 can be integrated with conversion layer 10 by one of the techniques that are indicated hereinafter.

Collection layer 20 is formed by a matrix of collection pixels 22, each of which is configured for receiving an amount of electrons from conversion layer 10, thus building up an electric charge on an own metal pad, not shown.

In this exemplary embodiment, collection pixels 22 have a regular hexagon plan shape, and are arranged to form a honeycomb pattern, in which each hexagon 22 generally lies beside six hexagons 22, each having a side parallel to a respective side of first hexagon 22.

Collection layer 20 is made in the form of a CMOS ASIC, i.e. an ASIC whose functional blocks consist of CMOS transistors.

Figure 2:
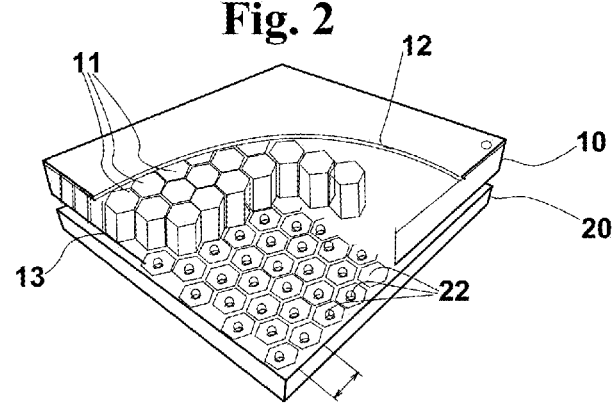
FIG. 2 shows an exemplary embodiment of the sensor.
Figure 3:
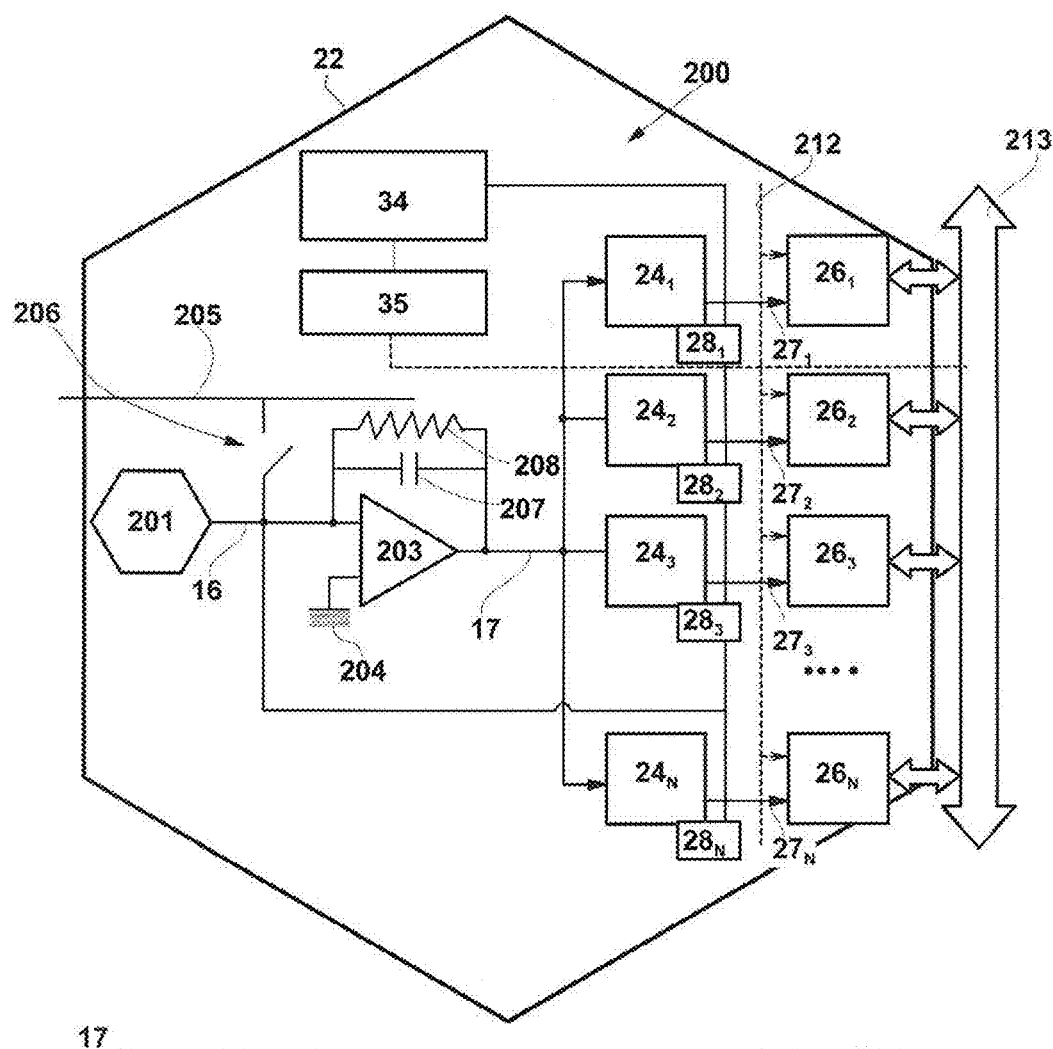
FIG. 3 is a distribution diagram of CMOS elements in a pixel, for carrying out an acquisition of images by the sensor according to the invention.
Figure 3A:
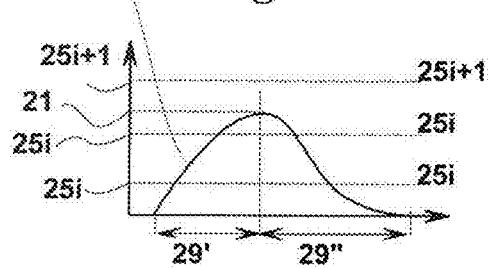
Figure 3B:
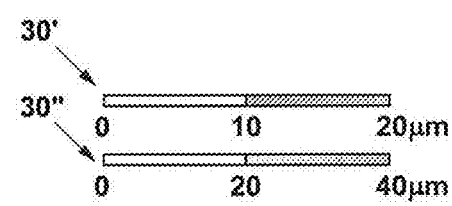

With reference to FIG. 2, each collection pixel 22 contains an electronics 200, equipped with a contact, e.g. a pad 201, for receiving charge 16 from a portion of collection layer 10.

Pad 201 is connected with an amplifier 203, such that charge 16 is collected by pad 201 and can be amplified by charge amplifier 203. Amplifier 203 produces a voltage signal 17 that, as shown in FIG. 2A, has a predetermined rise time 29' and a predetermined drop time 29'', and a voltage peak value 21 that is proportional to inlet electric charge 16. This way, each voltage peak value 17 represents one photon event, and the peak value is proportional to an energy value associated with this X-photon.

A capacitor means 207 is arranged parallel to amplifier 203 in order to transform charge 16 into current 17. A resistive element 208 lets condenser 207 to be periodically discharged.

Electronics 200 also comprises N window discriminators $24_i$, i=1 . . . N, each of which is configured for comparing voltage peak value 21 with a respective lower threshold value $25_i$ and with a respective upper threshold value, $25_{i+1}$, where $25_i < 25_{i+1}$. Each discriminator $24_i$ is also configured for generating a transition signal $27_i$ that causes a counter $26_i$ associated with discriminator $24_i$, typically a 15-bit counter, to increase by 1 unit, if the condition $25_i < 21 < 25_{i+1}$ occurs.

In particular, according to the invention, the upper threshold voltage value $25_i$ of discriminator $24_i$ coincide with the lower threshold voltage value of discriminator $24_{i+1}$, for all the values of i or for a part of them, such that a plurality of energy windows is formed that are all or in part adjacent.

In other words, the CMOS circuit that is contained in each collection pixel 22 is configured for comparing the value of charge 16, collected after converting photon 2 in conversion layer 10, with each thresholds $25_i$ of discriminators $24_i$. If charge 16 produces a signal 17 that has a peak value 21 higher than threshold $25_i$ and lower than threshold $25_{i+1}$, only counter $26_i$ increases its own count by 1 unity, while the other counters $26_j$, j≠i, maintain their respective counts unchanged.

This way, radiography sensor 100 can perform a chromatic photon-counting procedure, i.e. it allows measuring incident radiation 2 according to N "colours" which correspond to the counts stored in N energy windows $26_i$ [$25_i$, $25_{i+1}$], where i is an integer number set between 1 and N.

Collection pixels 22 may have a size shorter than 300 μm, for example a size selected from the group consisting of: 50, 100 and 200 μm. In exemplary specific embodiments, these pixel have a number of discriminators and of counters suitable for implementing two, four, eight energy windows, i.e. N=2, 4, 8, respectively. In particular, the number of windows is allowed by a 0.18-μm CMOS technology. If a 0.045-μm technology is used for the ASICs, pixel of the above indicated sizes may be used for making eight, sixteen, thirty-two energy windows, i.e. N=8, 16, 32, respectively.

Each counter $26_i$ is controlled by a common shutter signal 212 that defines the time interval during which the device is active. This signal ensures exposure times with a microsecond precision, as it is required for high frame rate acquisitions for "slot-running" type acquisitions.

The count values for each collection pixel 22 and for each energy window $26_i$ [$25_i$, $25_{i+1}$] are read by an external acquisition electronics 50 (FIG. 1) that receives them through a data output means such as a digital readout and control bus 213. Acquisition electronics 50, which can be conventionally implemented, is configured for forming an image $3_i$ for each energy window [$25_i$, $25_{i+1}$]. Each image $3_i$ may be made accessible to an observer through a conventional display means 7 (FIG. 1).

Acquisition electronics 50 may be configured for associating the count values of a same energy window $26_i$ with a grey level or, more in general, with a light level. This way, the count values of a same energy window, related to pixel 22, can be turned into an image $3_i$ in which the grey level or the bright-dark light level indicates the portion of radiation 2, i.e. of photons 2, that has an energy within a given window energy, which travels across an observed sample 9.

Acquisition electronics 50, or display means 7, is provided with a means for associating a window energy with a respective basic colour, such that the data pertaining to each energy windows are shown, in each image $3_i$, as different levels of a same basic colour.

Acquisition electronics 50, or display means 7, has means for overlapping images $3_i$, to form at least one or more new images, not shown, in which the data pertaining each energy window $26_i$ can be recognized by the respective basic colour, while the data pertaining the only energy windows can be recognized in the image as different levels of the basic colours.

Still in the exemplary embodiment of FIG. 2, electronics 200 of each collection pixel 22 comprises a charge supply means i.e. a "charge injection" means 205, 206 for supplying a charge to amplifier 203. The charge injection may be used for establishing the response of electronics 200 to a calibrated amount of charge. More in detail, as described hereinafter, the charge supply means is used for feeding, during an operation, a predetermined correction or compensation direct current that has a specific value for each collection pixel 22, in order to put aside the above-mentioned "dark" or offset current effects, so that pixel 22 of collection layer 20 can provide a homogeneous response. Charge supply means 206 is also used for determining the correction current for each pixel.

In fact, in each collection pixel 22, a calibration means is provided for calibrating the reference voltage of the signals supplied to discriminators $24_i$.

In the exemplary embodiment of FIG. 2, the self-calibration means of each collection pixel 22 of collection layer 20 comprises a digital-to-analog converter $28_i$ (DAC) for each unit discriminator/counter unit $24_i/26_i$. Each digital-to-analog converter $28_i$ is configured for receiving combinations of a predetermined number of bits, and for generating current values that correspond to said combinations of bits. Typically, DAC $28_i$ is a 5-bit DAC, which allows 32 combinations and, therefore 32 current values. DAC $28_i$ can be adjusted to provide a current suitable for displacing the reference of signal 21 as close as possible to the ground value, for instance, according to the procedure described in detail hereinafter.

According to the invention, a logical means 34 is arranged within each pixel 21, said means configured for performing an iterative procedure of computing an offset correction current. Normally, this iterative procedure comprises generating a plurality of trial current values for each discriminator/counter unit $24_i/26_i$, which are supplied in turn to amplification means 203 until a current value is identified that does not cause the counting $26_i$ to increase. This current is defined as the offset correction current. Logical means 34 is functionally connected to DAC $28_i$ for controlling the generation of the current trial values.

Still according to the invention, a memory unit, i.e a register 35, is also arranged within each pixel 22, and is functionally connected with logical means 34, wherein logical means 34 memorizes the offset correction current values that are defined during the self-calibration procedure, and that are available for the subsequent radiographic acquisitions. Memory unit 35 may also be advantageously connected with data output means 213 so that the correction current value can be read from outside, for statistic purposes or for adjusting/optimizing the required correction range.

Figure 4:
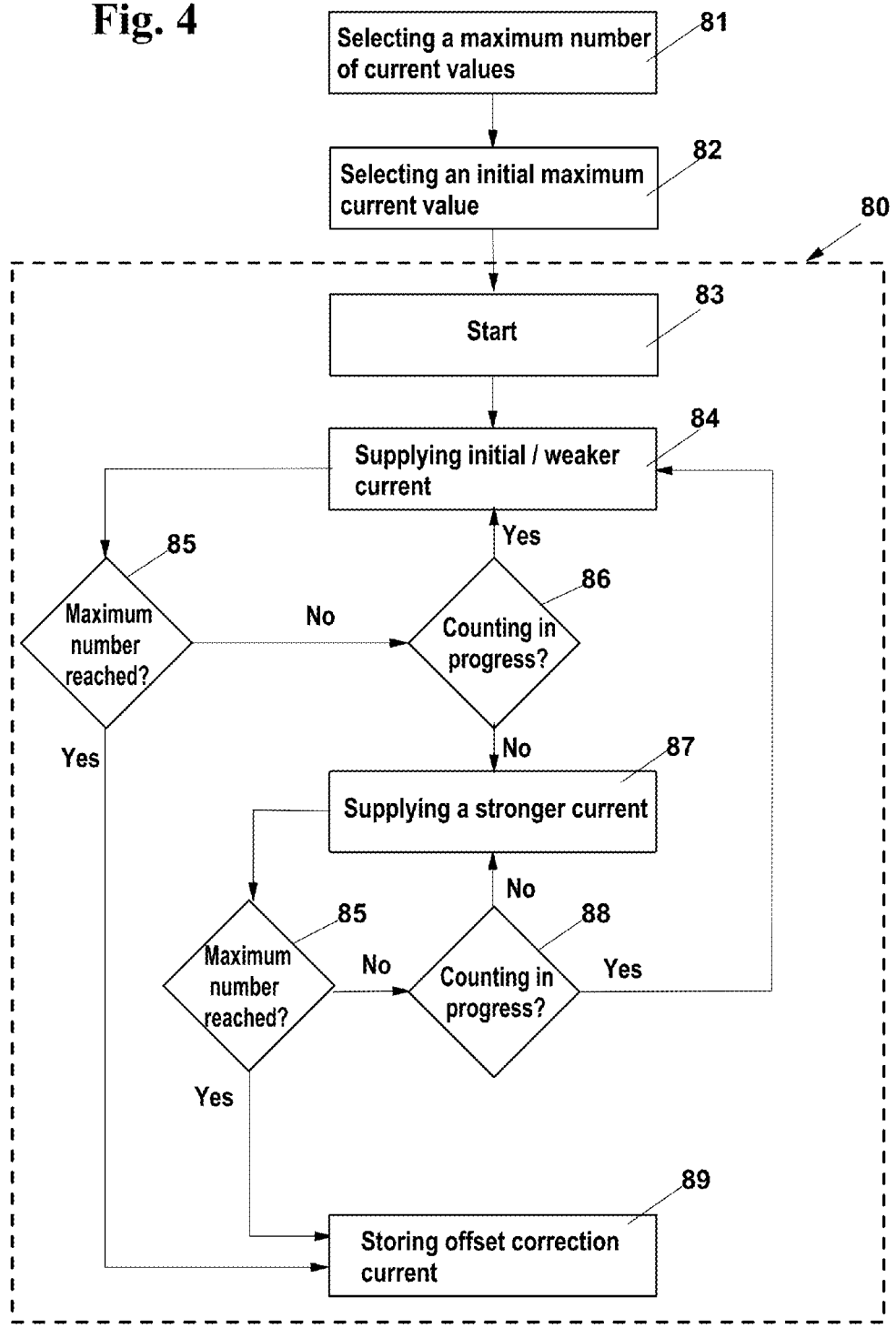
FIG. 4 shows a block diagram of a self-calibration procedure, which is carried out at the same time for all the pixel.

In particular, logical means 34 may be configured for performing a self-calibration procedure 80, i.e. a high/low automatic and contemporaneous calibration procedure of all counters $26_i$, as shown in the diagram of FIG. 4.

In summary, self-calibration procedure 80 comprises sequentially supplying currents of different intensities to each counter $26_i$, and assessing which is the supplied current value next to the value that makes it possible to overcome the specific offset value of each counter, in specific environmental operating conditions. By supplying this current during a subsequent operation, the counters of all the pixel will be able to provide a substantially homogeneous charge-counting response.

More in detail, self-calibration procedure 80 follows a step 81 of selecting a maximum number of current intensity values to be supplied. As many values are possible as the number of combinations that can be formed with the bit number of the DAC, therefore, by a 5-bit DAC, 32 different current intensities can be supplied to each discriminator $24_i$, whenever procedure 80 is carried out.

Procedure 80 also follows a step 82 of selecting an initial current value that, as suggested by previous tests or experiments, is adapted to shift the offset of all counters $26_i$ above the lower threshold value. By supplying this initial current, all counters $26_i$ will respond by increasing the count value by 1 unit.

Moreover, the self-calibration means comprises a control means of a step 83 of starting substantially at the same time the self-calibration procedure for preferably all the counters $26_i$ of all collection pixels 22, such that a calibration takes place simultaneously in each counter $26_i$.

Self-calibration means $28_i$ is configured for subsequently carrying out a step 84 of supplying at least one trial current to each counter $26_i$. The trial currents have a lower or a decreasing intensity, starting from the initial value selected in step 82. Steps 85 are also provided of checking whether a maximum number of iterations has been attained, as predefined in step 81, i.e. the number of currents of different intensity that, according to procedure 80, can be applied to discriminators/counters CMOS $24_i/26_i$ at each operation. Along with the check step 85, for each counter $26_i$ a step 86 is carried out of checking whether the counter is still carrying out a step of counting or not. If the counting is being carried on, a current weaker than the previous one is supplied to each counter, i.e. step 84 of supplying current is repeated, whereas, if the counting has been discontinued, a step 87 is carried out of supplying at least one current of intensity higher than the previous one. Even in this case, whenever current 84, 87 is supplied, a step 85 is carried out of checking the number of all the currents that have been supplied to each counter, along with a step 86, 88 of checking whether the counting is still being carried out by the converter or not. In the case of persistence of the counting value, a current of intensity higher than the previous one is supplied to each counter, i.e. current supply step 87 is repeated, while if the counting is re-started, a step 84 is carried out of supplying a current weaker than the previous one.

When check step 85, which is carried out after each current supply step 84,86, reveals that a counter $26_i$ has been supplied with a number of currents equal to a predetermined maximum number, the intensity of the last supplied current is recorded as the offset correction current of that specific counter $26_i$, in a step 89 of current value storing, for a subsequent operation of sensor 100.

As well known, CMOS technology is a layer technology, in which the transistor are arranged upon the so-called "metal 1" or "top metal layer", while the other layers, normally four or five metal layers, besides the transistor layer, are used to provide connections between the functional blocks and to deliver the power. FIGS. 7-11 diagrammatically show a lay-out of the functional blocks, implemented by transistors arranged on level 1.

Figure 5:
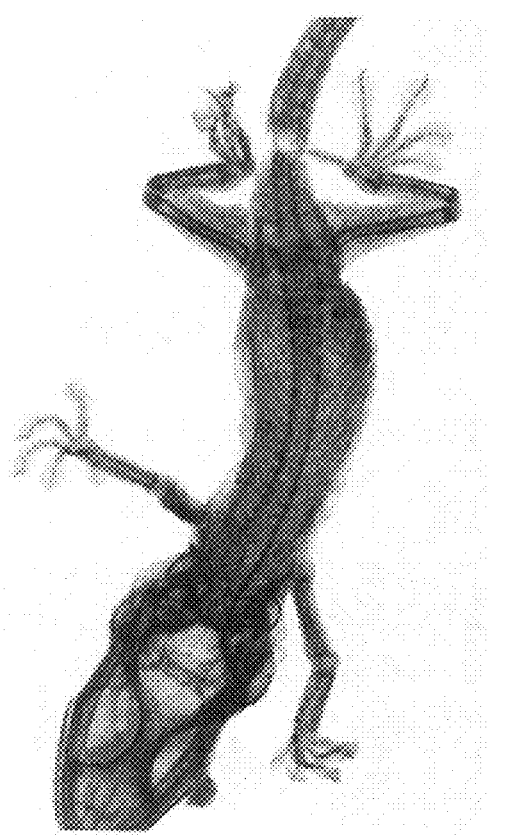
FIGS. 5 and 6 show two different images of a same sample, obtained in a radiographic session in which the sensor according to the invention is used.
Figure 6:
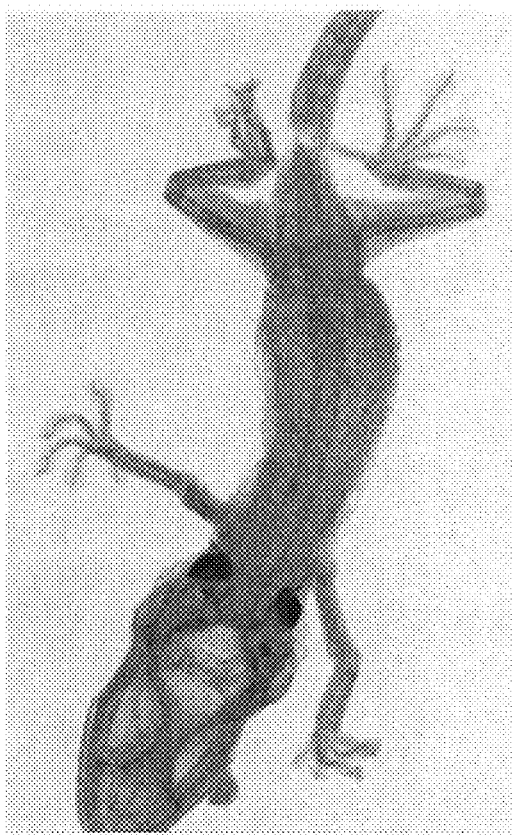

FIGS. 5 and 6 show two images of a sample consisting of a lizard, obtained by a sensor according to the invention. The images of FIGS. 5 and 6 refers to two different energy windows, respectively to an upper energy window and to a lower energy window.

Figure 7:
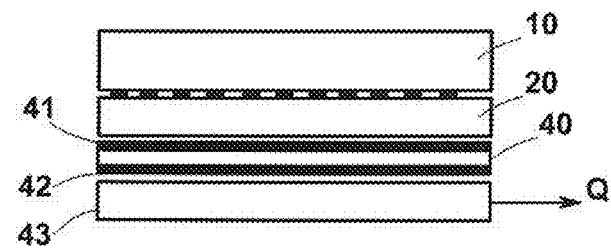
FIG. 7 shows a sensor, according to an exemplary embodiment of the invention, which has a cooling means, in particular, on the conversion layer.

With reference to FIG. 7, a digital X-ray sensor is described, according to an exemplary embodiment, which is provided with a cooling means 40 comprising a Peltier cell device 40 that has a cold face 41 in contact with collection layer 20 and a hot face 42 exposed to a means 43 for removing heat Q.

Figure 8:
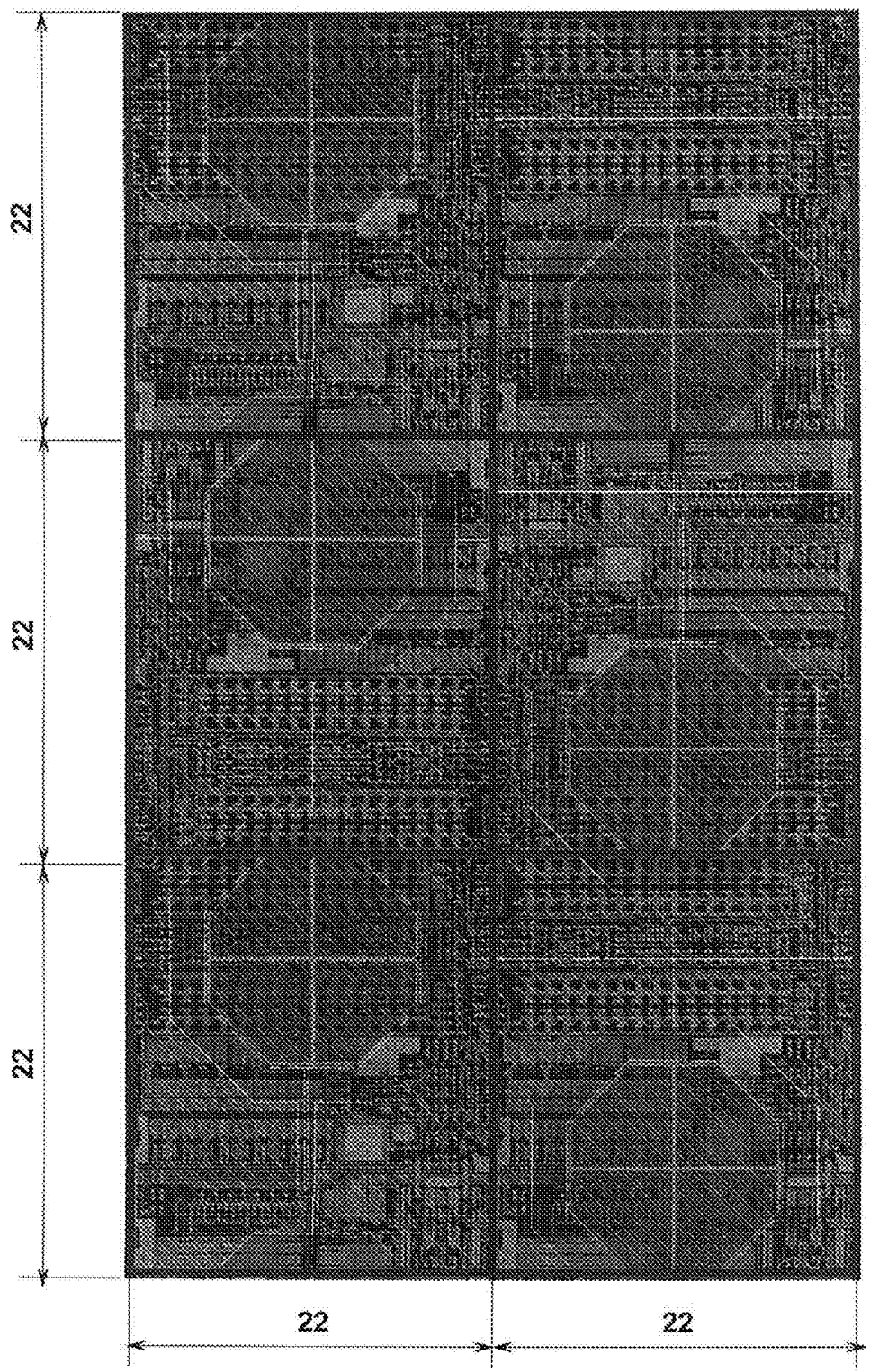
FIGS. 8-12 diagrammatically show the layout of the electronics of the collection pixels.

FIG. 8 is an overall view of a submatrix of 3×2 pixels, which also shows inlet pad 201 of pixel 22 made of the top metal layer. In an exemplary embodiment, on this pad 201 a bump is grown for connecting conversion layer 10 by the bump-bonding technique, for instance by using an Indium-Bismuth alloy. The electronic that relates to a single pixel is contained in the boundary frame.

Figure 9:
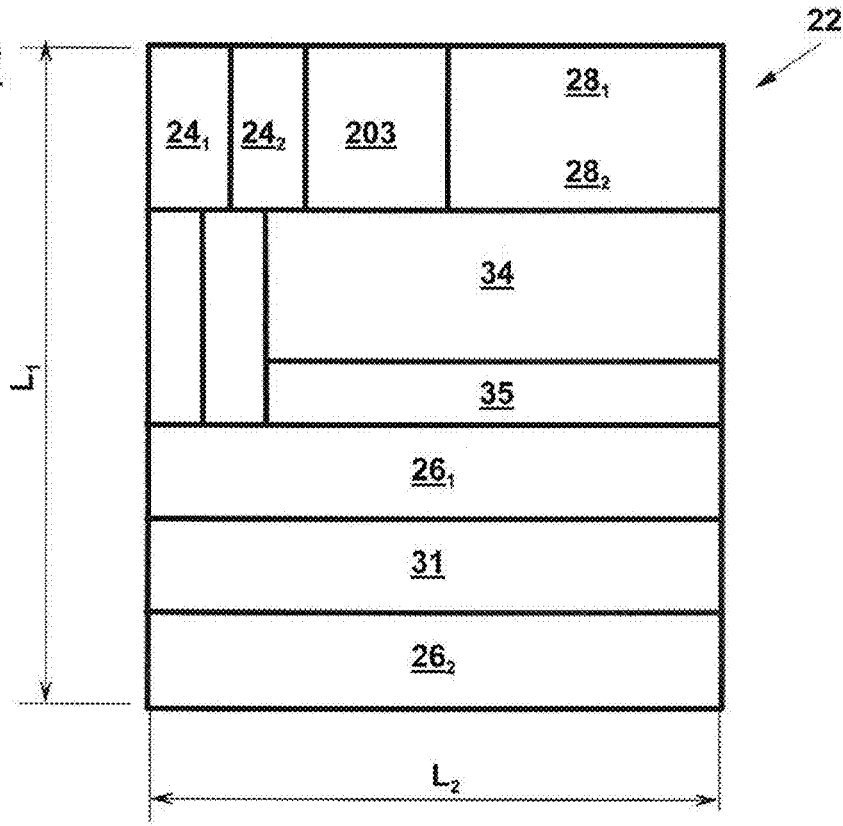
Figure 10:
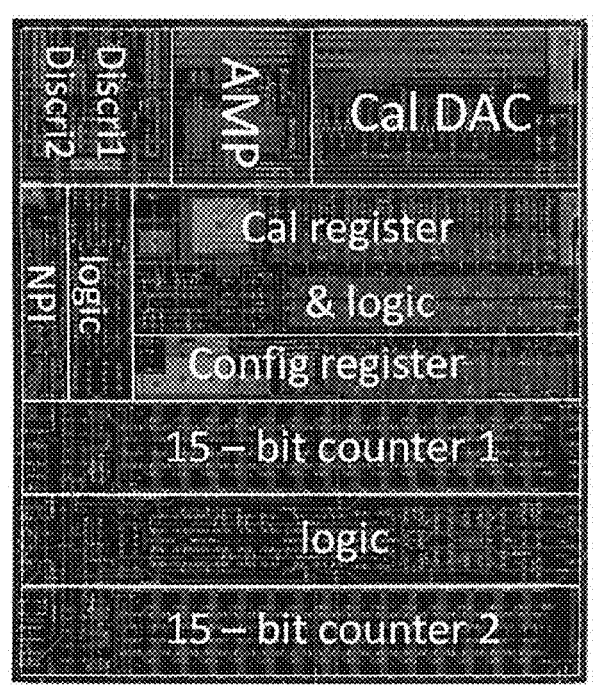

FIGS. 9 and 10 show a detail of one pixel 22 of FIG. 8, which has sizes $L_1$, $L_2$ of about 50 µm. Two energy window are implemented in each pixel, for example, by 0.18-µm CMOS technology. The functional blocks are arranged on the top metal layer, in particular amplifier 203, discriminators $24_1$ and $24_2$, counters $26_1$ and $26_2$, DACs $28_1$ and $28_2$, the logic 34, memory unit 35 (FIG. 9) are shown. In FIG. 10, the layers below the top metal layer are also shown.

Figure 11:
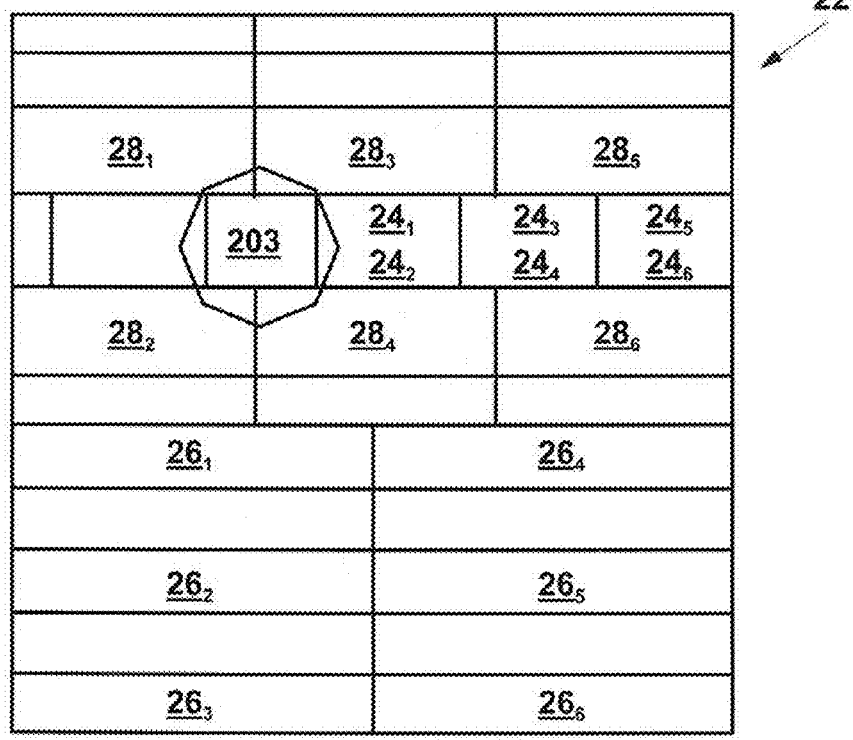
Figure 12:
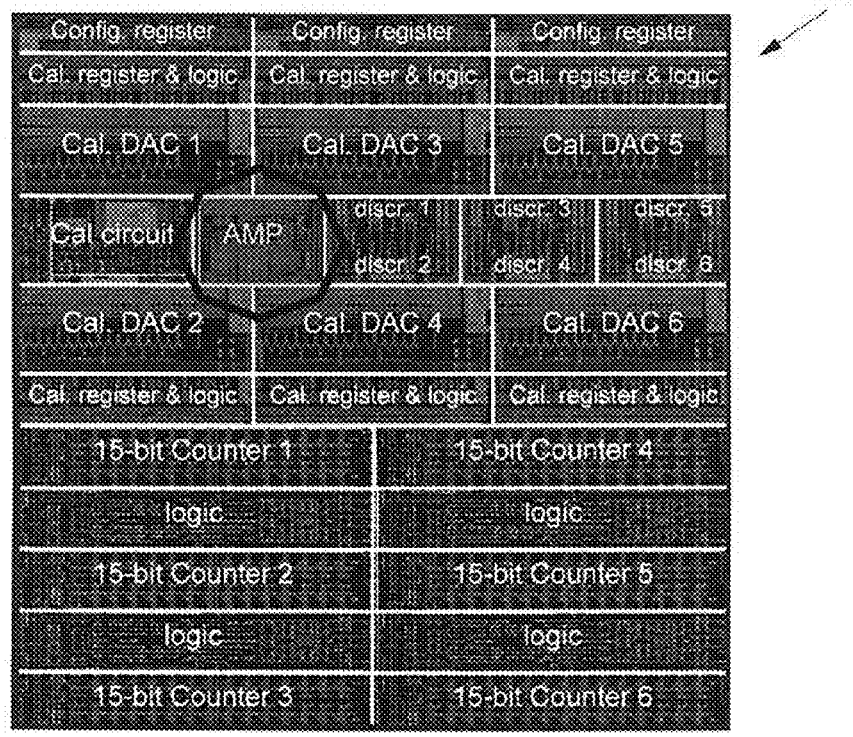

Instead, FIGS. 11 and 12 refer to a 100 µm pixel 22, in which the same functional blocks $24_i$, $26_i$, $28_i$, 203, i=1 . . . 6, are provided as in the 50 µm pixel of FIGS. 9 and 10, and where a six colours architecture is implemented in each pixel, still by a standard CMOS technology.

In the exemplary embodiment of FIG. 2, thin metallization films 12 and 13 are provided on the upper face and on the lower face of conversion layer 10, respectively. Thin film 12 may be made by a deposition of a conductive material, preferably a metal such as Platinum, and serves as an electrode. Thin film 12 is electrically connected to a voltage source 4, i.e. it is electrically connected to an element that is at a predetermined electric voltage, for example a voltage set between −300 and −400 V.

A metallization film 13 is laid upon the opposite face, which may be made in the form of a Schottky junction, i.e. in the form of a diode, so that the current of electrons can flow in one direction only, i.e. towards collection layer 20. More in detail, junction 13 may comprise a plurality of metallization levels, for instance two layers of metals that have an electrochemical potential different form each other, in order to form a barrier that can be trespassed by charges that have one predetermined sign, and that cannot be trespassed by charges that have the opposite sign. This way, it is possible to reduce the thermal loss current to a minimum value, which is due to the working temperature of ASIC 20.

In turn, junction 13 is electrically connected to the voltage, between 0.1 V and 1.0 V, of the pads of the pixel of the ASIC, which is supplied by a voltage source 5.

The voltages applied to thin films 12 and 13 create an electric field in conversion layer 10, said field adapted to cause a migration of the electrons that are generated by photon conversion in conversion layer 10, towards collection layer 20.

With reference to FIG. 2, also conversion layer 10 of the X-ray sensor may be formed by a plurality of conversion pixels 11, in particular, according to a pattern identical to collection pixels 22. In this case, advantageously, each collection pixel 22 of collection layer 20 is electrically connected with a respective conversion pixel 11 of conversion layer 10, in such a way that each collection pixel 21 computes charge 16 coming from the respective conversion pixel 11.

Conversion layer 10 may comprise either a crystalline or an amorphous material. For instance, conversion layer 10 may be obtained by an evaporation technique and/or by a deposition technique of a polycrystalline or amorphous semiconductor material selected, for example, between Cadmium telluride; amorphous Selenium; Lead iodide; Mercuric iodide. If conversion layer 10 must be subdivided into pixel, the division can be carried out by resorting to photolithographic techniques.

In the exemplary embodiment of FIG. 1, conversion layer 10 is connected with collection layer 20 by a bump-bonding technique. According to this technique, a plurality of metal bumps 23, obtained for example by a growth procedure carried out on semiconductor collection layer 20, is arranged between conversion layer 10 and collection layer 20. In particular, bumps 23 may comprise an Indium-Bismuth alloy.

The foregoing description of various exemplary specific embodiments will so fully reveal the invention according to the conceptual point of view, so that others, by applying current knowledge, will be able to modify and/or adapt for various applications such embodiment without further research and without parting from the invention, and, accordingly, it is meant that such adaptations and modifications will have to be considered as equivalent to the exemplary embodiments described. The means and the materials to realise the different functions described herein could have a different nature without, for this reason, departing from the field of the invention. It is meant that the phraseology or the terminology that is employed herein is for the purpose of description and not of limitation.

REFERENCES

[1] Sindre Mikkelsen Et Al: "An ASIC for multi-energy x-ray counting", Nuclear science symposium conference record, 2008. NSS '08. IEEE (19-25 Oct. 2008), IEEE, Piscataway, N.J., USA, 19 Oct. 2008, pp. 1996-2001, XP031419139, ISBN: 978-1-4244-271 4-7

[2] Roberto Dinapoll ET AL: "EIGER: Next generation only photon-counting detector for X-ray applications", Nuclear instruments & methods in physics research. Section A: Accelerators, spectrometers, detectors, and associated equipment, vol. 650, n. 1, 201 1, pp. 79-83, XP028273505, ISSN: 0168-9002, DOI: 10.1 01 6IJ. NIMA. 2010.12.005 [retrieved on 2010-12-141]

[3] Radicci V. Et al: "EIGER to in the only photon-counting detector for X-ray applications: performance of the chip", Journal of instrumentation, institution of physics publishing, Bristol, GB, vol. 7, n. 2, 9 Feb. 2012, page C0201 9, XP020218873, ISSN: 1748-0221, DOI: 10.108811/748-0221/7/02/C02019

[4] Matteo Perenzoni et al: "A Multispectral Analog Photon-Counting Readout Circuit for X-ray Hybrid Pixel Detectors", IEEE Transactions on instrumentation and measurement, IEEE Service Centre, Piscataway, N.J., US, vol. 57, n. 7, 1° July 2008, pp. 1438-1444, XP011205122, ISSN: 001 8-9456

The invention claimed is:

1. A digital X-ray sensor (100) comprising:
a semiconductor conversion layer (10), configured for receiving X-ray photons (2) and for converting said X-ray photons (2) into an electric charge (14);
a semiconductor collection layer (20) integrated with said conversion layer (10), said collection layer (20) formed by a plurality of collection pixels (22) that are arranged in a predetermined pattern, each collection pixel (22) of said collection layer (20) configured for receiving electrons (16) of said electric charge (14) from said conversion layer (10);
a data output means (213) for transferring data collected by said collection pixels (22) to an acquisition electronics (50);
wherein each collection pixel (22) comprises:
an amplification means (203) arranged for receiving said electric charge as an inlet charge, which comprises said electrons (16) produced by said conversion layer (10), said amplification means (203) configured for generating a voltage signal (17) that has a peak value (21) proportional to said inlet electric charge (16);
a plurality of N window discriminators (24$_i$), each discriminator (24$_i$) comprising a plurality of CMOS transistors, each discriminator (24$_i$) configured for:
carrying out a comparison between said peak value (21) and two charge threshold values (25$_i$, 25$_{i+1}$) comprising a lower threshold value (25$_i$) and an upper threshold value (25$_{i+1}$), and
carrying out an instantaneous transition between a 0-level and an 1-level if:
said peak value (21) is higher than said lower threshold value (25$i$), and
said peak value (21) is lower than said upper threshold value (25$_{i+1}$);
wherein, for each discriminator (24$i$), at least one condition occurs that is selected between:
said upper threshold value (25$_{i+1}$) is lower than said lower threshold value of at least one of said discriminators (24$_k$,k≠i) distinct from said each discriminator (24$_i$), in particular said upper threshold value (25$_{i+1}$) is equal to said lower threshold value of said at least one of said discriminators (24$_k$,k≠i) distinct from said each discriminator (24$_i$);
said lower threshold value (25$_i$) is higher than said lower threshold value of at least one of said discriminators (24$_k$,k≠i) distinct from said each discriminator (24$_i$), in particular said lower threshold value (25$_i$) is equal to said upper threshold value of said at least one of said discriminators (24$_k$,k≠i) distinct from said each discriminator (24$_i$),
wherein each collection pixel (22) comprises a plurality of N counters (26$_i$), each of said counters (26$_i$) associated with a respective discriminator of said discriminators (24$_i$),
wherein each counter (26$_i$) is configured to increase by 1 unit a value of an own counting if:
said peak value (21) is higher than said lower threshold value (25$_i$) of said respective discriminator (24$i$), and
said peak value (21) is lower than said upper threshold value (25$_{i+1}$) of said respective discriminator (24$_i$),
while said counters (26$_k$,k≠i) distinct from said each counter (26$_i$) are configured for keeping unchanged an own count value,
wherein said data output means (213) is configured for receiving from said counters (26$_i$) of each collection pixel (22) measurement data of the radiation (2) incident in N "colours" corresponding to the counts stored in N energy windows for each charge threshold,
characterized in that it comprises:
a digital-to-analog converter (DAC) (28$_i$) for at least one discriminator (24$_i$) of each collection pixel (22), said digital-to-analog converter (28$_i$) configured for receiving combinations of a predetermined number of bits and for generating current values corresponding to said combinations of bits;
a current supply means (206) for supplying a current to each collection pixel (22), configured for supplying a current to said amplification means (203) responsive to said combinations of bits of said at least one discriminator (24$_i$);
a logical means (34) resident in each of said collection pixels (22), configured for determining an offset correction current value, said logical means configured for carrying out a calibration step within each collection pixel in order to establish which combination of bits of said combinations of bits of said or each digital-to-analog converter (28$_i$) has to be used for supplying said correction current, said calibration step preliminarily carried out in each pixel by said logical means (34) at the same time for all said collection pixels (22),
wherein each of said collection pixels (22) comprises a memory unit (35) of said offset correction current value;
and wherein said logical means (34) is also configured for storing said correction current value into said memory unit (35).

2. The digital sensor according to claim 1, wherein said logical means, which is resident in each of said collection pixels (22), is configured for carrying out said calibration step within each collection pixel by an iterative procedure (80) of computing said offset correction current value, said procedure comprising:
generating said combinations of bits;
transferring said combinations of bits to said digital-to-analog converter (28$_i$) such that said digital-to-analog converter (28$_i$) generates a corresponding trial current value;
causing said trial current to be supplied to said amplification means (203) through said supply means (206);
receiving a count value of said counter (28$_i$);
repeating the above steps if said count value increases due to said trial current;

defining said trial current value as said correction current value if said count value does not increase due to said trial current.

3. The digital sensor according to claim 1, wherein said trial current has a value that decreases at each iteration of said steps of said iterative procedure (80), starting from an initial trial current value adapted to cause a count event in each discriminator/counter unit ($24_i/26_i$), until a final trial current value is attained that does not cause a count event in said discriminator/counter unit ($24_i/26_i$), and said logical means of each collection pixel (22) is configured for defining said final trial current value as said correction current value of said collection pixel (22) in said memory unit (35) of said collection pixel (22).

4. The digital X-ray sensor according to claim 1, wherein said collection pixels (22) have a hexagonal plan shape, and are arranged in a honeycomb pattern.

5. The digital X-ray sensor according to claim 1, wherein said digital-to-analog converter ($28_i$) has a bit number higher than or equal to 5, in particular said digital-to-analog converter ($28i$) is a 5-bit digital-to-analog converter.

6. The digital X-ray sensor according to claim 1, wherein said lower charge threshold values ($25_i, 25_{i+1}$) of said discriminators ($24_i$) are selected in such a way that photons energy fields, i.e. photons energy windows are defined selected from the group consisting of: 5 to 15 keV; 15 to 25 keV; 25 to 40 keV; 40 to 60 keV.

7. The digital X-ray sensor according to claim 1, wherein said counters ($26_i$) comprise ordinary 15-bit silicon registers.

8. The digital X-ray sensor according to claim 1, wherein said sensor has side dimensions set between 2 and 4 cm, in particular dimensions of about 2.5×3.0 cm.

9. The digital X-ray sensor according to claim 1, wherein said collection pixels (22) have a size set between 300 μm and 25 μm, in particular they have a size set between 150 μm and 25 μm, more in particular, they have a size set between 75 μm and 25 μm.

10. The digital X-ray sensor according to claim 9, wherein said CMOS transistors are 0.18-μm CMOS transistors, and said collection pixels have a size of about 200 μm and comprise a number of said discriminators ($24_i$) and of said counters ($28_i$) such that eight energy windows are defined.

11. The digital X-ray sensor according to claim 9, wherein said CMOS transistors are 0.18-μm CMOS transistors, and said collection pixels have a size of about 100 μm and comprise a number of said discriminators ($24_i$) and of said counters ($28_i$) such that six energy windows are defined.

12. The digital X-ray sensor according to claim 9, wherein said CMOS transistors are 0.18-μm CMOS transistors, and said collection pixels have a size of about 50 μm and comprise a number of said discriminators ($24_i$) and of said counters ($28_i$) such that two energy windows are defined.

13. The digital X-ray sensor according to claim 9, wherein said CMOS transistors are 0.045-μm CMOS transistors, and said collection pixels have a size of about 200 μm and comprise a number of said discriminators ($24_i$) and of said counters ($28_i$) such that thirty-two energy window are defined.

14. The digital X-ray sensor according to claim 9, wherein said CMOS transistors are 0.045-μm CMOS transistors, and said collection pixels have a size of about 100 μm and comprise a number of said discriminators ($24_i$) and of said counters ($28_i$) such that sixteen energy windows are defined.

15. The digital X-ray sensor according to claim 9, wherein said CMOS transistors are 0.045-μm CMOS transistors, and said collection pixels have a size of about 50 μm and comprise a number of said discriminators ($24_i$) and of said counters ($28_i$) such that eight energy windows are defined.

16. The digital X-ray sensor (100) according to claim 1, wherein said semiconductor conversion layer (10) comprises a plurality of conversion pixels (11) arranged in a pattern corresponding to the pattern of the collection pixels (22) of said collection layer (20), wherein each conversion pixel (11) univocally corresponds to a respective collection pixel (11), and an electric connection is provided between each conversion pixel (11) and said respective collection pixel (22).

17. The digital X-ray sensor according to claim 1, wherein the conversion layer (10) is made of a crystalline material.

18. The digital X-ray sensor according to claim 5, wherein said crystalline material has a metallization layer (13) facing said collection layer (10) which has a pixel structure (11).

19. The digital X-ray sensor according to claim 5, wherein the pixels (11) of said conversion layer (10), which face said pixels (22) of said collection layer (20), are obtained by a photolithographic technique, in particular by deposition and patterning of thin semiconductor and insulating metal films.

20. The digital X-ray sensor according to claim 1, wherein said conversion layer (10) is joined pixel-by-pixel (11-22) with said collection layer (20) by a bump-bonding technique, i.e. through a plurality of bumps (23) made of an electrically conductive material, which are located between the conversion layer (10) and the collection layer (20), wherein each bump (23) is arranged at a respective collection pixel (22).

21. The digital X-ray sensor according to claim 1, wherein said conversion layer (10) is obtained by coating said collection layer (20) by an evaporation and deposition technique, in particular by a screen-printing technique, of a polycrystalline or amorphous semiconductor material on said collection layer (20).

22. The digital X-ray sensor according to claim 1, wherein said conversion layer (10) comprises a material selected from the group consisting of: Cadmium telluride; Selenium; Lead iodide; Mercuric iodide; Gallium arsenide; Germanium or a combination of said materials.

23. The digital X-ray sensor according to claim 1, wherein a conversion layer (10) cooling means is provided that is configured for bringing and maintaining said conversion layer (10), in use, to/at a temperature lower than a predetermined maximum operation temperature, in particular the cooling means is configured for bringing and maintaining said conversion layer between 20° C. and 40° C., in particular, said cooling means comprises a Peltier cell device that has a cold face in contact with said collection layer (20) and a hot face exposed to a heat removal means.

24. The digital X-ray sensor according to claim 1, wherein said collection layer (20) has a conductive pad (33), in particular an aluminium pad, for each collection pixel, in particular said pad (33) forms an interface towards said charge amplification means (203), which forms the inlet stage of the electronics (200) of each pixel (22).

25. The digital X-ray sensor according to claim 11, comprising a means (4,5,12,13) for creating an electric field within said collection layer (20), said means comprising:

a first metal thin film (12) arranged about said sensor (100) and configured for being brought to a first predetermined voltage, and a second thin film (13) arranged upon the conversion layer (10) at the side connected to said collection layer (20), said second thin film configured for being brought to a voltage of said inlet pads (33) of said conversion layer (10).

26. The digital X-ray sensor according to claim 12, wherein said second thin film (13), in particular along with further metal films deposited on the same face of said conversion layer (20), is configured to provide a Schottky type junction.

27. A radiographic imaging method by an X-ray sensor (100), said method comprising:
irradiating a semiconductor conversion layer (10) with X-ray photons (2) and converting said X-ray photons (2) into an electric charge (14) by said conversion layer (10);
prearranging a semiconductor collection layer (20) integrated with said conversion layer (10), said collection layer (20) formed by a plurality of collection pixels (22) that are arranged in a predetermined pattern;
receiving electrons (16) of said electric charge (14) from said conversion layer (10) by each collection pixel (22) of said collection layer (20);
amplifying (203) said electric charge in each collection pixel (22), and producing a voltage signal (17) that has a peak value (21) proportional to said electric charge (16);
discriminating said peak value in each collection pixel (22) by a plurality of N window discriminators ($24_i$), each discriminator ($24_i$) comprising a plurality of CMOS transistors, wherein each discriminator ($24_i$):
performs a comparison between said peak value (21) and two charge threshold values ($25_i$, $25_{i+1}$) comprising a lower threshold value ($25_i$) and a upper threshold value ($25_{i+1}$), and
performs an instantaneous transition between a 0-level and a 1-level if:
said peak value (21) is higher than said lower threshold value (25i), and
said peak value (21) is lower than said upper threshold value ($25_{i+1}$);
wherein, for each discriminator (24i) at least one condition occurs selected between:
said upper threshold value ($25_{i+1}$) is lower than said lower threshold value of at least one of said discriminators ($24_k$,k≠i) distinct from said each discriminator ($24_i$), in particular said upper threshold value ($25_{i+1}$) is equal to said lower threshold value of said at least one of said discriminators ($24_k$,k≠i) distinct from said each discriminator ($24_i$);
said lower threshold value ($25_i$) is higher than said lower threshold value of at least one of said discriminators ($24_k$,k≠i) distinct from said each discriminator ($24_i$), in particular said lower threshold value ($25_i$) is equal to said upper threshold value of said at least one of said discriminators ($24_k$,k≠i) distinct from said each discriminator ($24_i$);

counting, in each collection pixel (22), the peak values discriminated at each discriminator by means of a plurality of N counters ($26_i$), each of said counters ($26_i$) associated with a respective discriminator of said discriminators ($24_i$),
wherein said counting in each counter ($26_i$) is carried out by increasing a value of an own counting by 1 unit, if:
said peak value (21) is higher than said lower threshold value ($25_i$) of said respective discriminator (24i) and
said peak value (21) is lower than said upper threshold value ($25_{i+1}$) of said respective discriminator ($24_i$),
while said counters ($26_k$,k≠i) distinct from said each counter ($26_i$) maintain unchanged an own count value,
acquiring, by a data output means (213), data collected by said collection pixels (22) for transmitting said data to an acquisition electronics (50);
characterized in that it comprises:
prearranging a digital-to-analog converter (DAC) ($28_i$) for at least one discriminator ($24_i$) of each collection pixel (22), said converter configured for receiving combinations of a predetermined number of bits and for generating current values corresponding to said combinations of bits;
supplying a correction current (206) to said amplification means (203) of each of said collection pixels (22), said current supplied responsive to said combinations of bits of said at least one discriminator ($24_i$);
and in that it also comprises a calibration step carried out within each collection pixel in order to establish which combination of bits of said combinations of bits of said or each digital-to-analog converter ($28_i$) has to be used for supplying said correction current, said calibration step carried out preliminarily in each pixel by a logical means (34) that is resident in each of said collection pixels (22);
wherein said calibration step is carried out within each collection pixel at the same time for all said collection pixels (22).

28. A radiographic imaging method according to claim 27, wherein said calibration step comprises an iterative procedure (80) of computing an offset correction current value, comprising:
generating said combinations of bits;
transferring said combinations of bits to said digital-to-analog converter ($28_i$) such that said digital-to-analog converter ($28_i$) generates a corresponding trial current value;
causing said trial current to be supplied to said amplification means (203) through said supply means (206);
receiving a count value of said counter (28i);
repeating the above steps if said count value increases due to said trial current;
defining said trial current value as said correction current value if said count value does not increase due to said trial current.

* * * * *